(12) United States Patent
Rao et al.

(10) Patent No.: US 7,943,015 B2
(45) Date of Patent: *May 17, 2011

(54) USE OF COPOLYMERS OF PERFLUORO(ALKYL VINYL ETHER) FOR PHOTOCHEMICAL REACTIONS

(75) Inventors: Velliyur Nott Mallikarjuna Rao, Wilmington, DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 353 days.

This patent is subject to a terminal disclaimer.

(21) Appl. No.: 11/792,642

(22) PCT Filed: Dec. 19, 2005

(86) PCT No.: PCT/US2005/046266
§ 371 (c)(1),
(2), (4) Date: Jun. 7, 2007

(87) PCT Pub. No.: WO2006/069107
PCT Pub. Date: Jun. 29, 2006

(65) Prior Publication Data
US 2008/0015277 A1    Jan. 17, 2008

Related U.S. Application Data

(60) Provisional application No. 60/638,290, filed on Dec. 22, 2004.

(51) Int. Cl.
*B01J 19/12* (2006.01)
*C07C 17/20* (2006.01)
*C07C 19/01* (2006.01)
*C07C 19/08* (2006.01)

(52) U.S. Cl. ........... 204/158.11; 204/157.94; 422/186.3; 570/123; 570/170; 570/260

(58) Field of Classification Search .................. 522/184, 522/185, 188; 422/131, 186, 186.3; 204/157.95, 204/157.94, 158.11; 250/492.1, 492.3; 570/123, 570/170, 260

See application file for complete search history.

(56) References Cited

U.S. PATENT DOCUMENTS

| | | | | |
|---|---|---|---|---|
| 3,554,887 A * | 1/1971 | Feehs | | 204/158.11 |
| 4,855,112 A | 8/1989 | Adcock et al. | | |
| 4,973,742 A * | 11/1990 | Ohsaka et al. | | 560/184 |
| 5,026,801 A * | 6/1991 | Krespan et al. | | 526/247 |
| 5,190,626 A | 3/1993 | Yates et al. | | |
| 5,258,561 A * | 11/1993 | Nappa et al. | | 570/169 |
| 5,350,821 A | 9/1994 | Feiring et al. | | |
| 5,414,165 A * | 5/1995 | Nappa et al. | | 570/169 |
| 5,750,808 A | 5/1998 | Cassel et al. | | |
| 5,872,157 A * | 2/1999 | DeSimone et al. | | 522/5 |
| 5,919,878 A | 7/1999 | Brothers et al. | | |
| 6,489,510 B1 | 12/2002 | Braun et al. | | |
| 7,009,017 B2 * | 3/2006 | Kurihara et al. | | 526/247 |
| 7,524,999 B2 * | 4/2009 | Nappa et al. | | 570/169 |
| 2007/0009403 A1 * | 1/2007 | Ehrfeld et al. | | 422/186 |
| 2007/0265368 A1 | 11/2007 | Rao et al. | | |
| 2008/0076950 A1 | 3/2008 | Rao et al. | | |
| 2008/0108853 A1 | 5/2008 | Nappa et al. | | |
| 2008/0149472 A1 | 6/2008 | Rao et al. | | |

FOREIGN PATENT DOCUMENTS

| | | |
|---|---|---|
| DE | 196 34 780 A1 | 3/1998 |
| EP | 0729932 | 4/1996 |
| WO | WO 97/24306 A1 | 7/1997 |
| WO | WO 02/93261 * | 1/2002 |
| WO | WO 03/068718 A2 | 8/2003 |
| WO | WO 03/097588 A2 | 11/2003 |
| WO | WO 2004/018093 A2 | 3/2004 |

OTHER PUBLICATIONS

R. Roberts et al., Applications of Photochemistry, 1984, pp. 27-30, Technomic Publishing Co. Inc.
E. Tschuikow-Roux et al., Photochlorination of Chloroethane and Chloroethane-d5, J. Phys. Chem., 1984, vol. 88:1408-1414.
Walling et al., The Relative Reactivities of Substituted Toluenes Toward Chlorine Atoms, J. Amer. Chem. Soc.; 1957, vol. 79:4181-4187.
P. Boule et al., Photodimerization of Maleic Anhydride in Carbon Tetrachloride, Tetrahedron Letters, 1976, vol. 11:865-868.
Journal of Fluorine Chemistry, "Modification of Perfluorinated Polymers by High Enegrgy", Klaus Lunkwitz et al, Dresden, Germany, 2004, pp. 863-873.

* cited by examiner

Primary Examiner — Susan W Berman

(57) ABSTRACT

A photochemical reaction apparatus including a reactor and a light source situated so that light from the light source is directed through a portion of the reactor wall is disclosed. The apparatus is characterized by the portion of the reaction wall comprising a copolymer of a perfluoro (alkyl vinyl ether). The perfluoro (alkyl vinyl ether) is selected from the group consisting of $CF_3OCF=CF_2$, $C_2F_5OCF=CF_2$, $C_3F_7OCF=F_2$, and mixture thereof. Also disclosed is a photochemical reaction process wherein light from a light source is directed through said reactor wall to interact with reactants in said reactor. A process for increasing the fluorine content of at least one compound selected from hydrocarbons and halohydrocarbons, comprising: (a) photochlorinating said at least one compound; and (b) reacting the halogenated hydrocarbon produced in (a) with HF. A process for producing an olefinic compound, comprising: (a) photochlorinating at least one compound selected from hydrocarbons and halohydrocarbons containing at least two carbon atoms and at least two hydrogen atoms to produce a halogenated hydrocarbon containing a hydrogen substituent and a chlorine substituent on adjacent carbon atoms; and (b) subjecting the halogenated hydrocarbon produced in (a) to dehydrohalogenation.

18 Claims, No Drawings

USE OF COPOLYMERS OF PERFLUORO(ALKYL VINYL ETHER) FOR PHOTOCHEMICAL REACTIONS

This application represents a national filing under 35 U.S.C. 371 of International Application No. PCT/US05/046266 filed Dec. 19, 2005, and claims priority of U.S. Provisional Application No. 60/638,290 filed Dec. 22, 2004.

FIELD OF THE INVENTION

This invention relates to the field of photochemical reactions, and particularly to materials suitable for use in photochemical reaction apparatus.

BACKGROUND OF THE INVENTION

Photochemical reactions use light as a source of energy to promote chemical processes. Ultraviolet (UV) and visible light are widely used in chemical synthesis both in laboratories and in commercial manufacturing. Well known photochemical reactions include photodimerization, photopolymerization, photohalogenation, photoisomerization and photodegradation. For example, cyclobutanetetracarboxylic dianhydride can be synthesized by photodimerization of maleic anhydride in a glass reactor using a mercury UV lamp (P. Boule et al., Tetrahedron Letters, Volume 11, pages 865 to 868, (1976)). Most of the vitamin D production in the United States is based on UV photolysis in a quartz vessel using light between 275 and 300 nm.

In photochlorination, chlorine ($Cl_2$) reacts with a saturated or unsaturated starting material, in the presence of a ultraviolet light source. This process is widely used to form carbon-chlorine bonds under mild conditions (e.g., room temperature) compared to the elevated temperatures normally required for thermal chlorination (R. Roberts et al., Applications of Photochemistry, TECHNOMIC Publishing Co., Inc. 1984). For example, E. Tschuikow-Roux, et al. (J. Phys. Chem., Volume 88, pages 1408 to 1414 (1984)) report photochlorination of chloroethane and Walling et al. (J. Amer. Chem. Soc., Volume 79, pages 4181 to 4187 (1957)) report photochlorination of certain substituted toluenes. U.S. Pat. No. 5,190,626 describes the use of photochlorination in removing unsaturated compounds such as vinylidine chloride from $CCl_2FCH_3$ product. Chlorine-containing compounds such as $CCl_2FCH_3$ may be readily converted to olefinic compounds (e.g., $CClF=CH_2$) by dehydrohalogenation or to fluorine-containing compounds (e.g., $CF_3CH_3$) by fluorination using hydrogen fluoride (HF).

Typically in photochlorinations, light from a suitable source (e.g., an incandescent bulb or a UV lamp) is directed through a reactor wall to interact with the reactants therein. The portion of the reactor wall through which the light passes must have a suitable transmittance to allow light of a wavelength required for the photochlorination to enter the reactor. Typically, quartz or borosilicate glass like Pyrex™ glass have been employed as transparent materials. Quartz is expensive, but has a low cut-off wavelength at about 160 nm; Pyrex™ glass is less expensive, but has a relatively high cut-off wavelength at about 275 nm. Due to their reactivity, quartz and Pyrex are not appropriate materials of construction for chemical reactions involving base or HF. There is a need for additional materials which can be used for this purpose in photochemical reactions (e.g., photochlorinations).

SUMMARY OF THE INVENTION

This invention provides an apparatus for photochemical reactions comprising a reactor and a light source situated so that light from the light source is directed through a portion of the reactor wall. In accordance with this invention, the apparatus is characterized by said portion of the reaction wall comprising a copolymer of a perfluoro(alkyl vinyl ether).

This invention also provides a photochemical reaction process wherein light from a light source is directed through a reactor wall to interact with reactants in said reactor. In accordance with this invention, the process is characterized by the light directed through the reactor wall being directed through a copolymer of a perfluoro(alkyl vinyl ether).

DETAILED DESCRIPTION

In accordance with this invention, copolymers of perfluoro (alkyl vinyl ethers) (such as PFA and Teflon® AF) are used as photochlorination reactor materials through which light is able to pass for the purpose of interacting with the reactants, thereby promoting the photochemical reaction. Suitable copolymers include copolymers of at least one perfluorinated alkylene monomer with a perfluoro(alkyl vinyl ether). Of note are copolymers of tetrafluoroethylene and/or hexafluoropropene with a perfluoro(alkyl vinyl ether). Suitable perfluoro(alkyl vinyl ethers) include $CF_3OCF=CF_2$, $C_2F_5OCF=CF_2$, and $C_3F_7OCF=CF_2$. Suitable copolymers include copolymers of $CF_3OCF=CF_2$, $C_2F_5OCF=CF_2$, and/or $C_3F_7OCF=CF_2$ with perfluorinated alkylene monomers. PFA is a copolymer of tetrafluoroethylene and a perfluoro(alkyl vinyl ether) where the alkyl group is $—CF_3$, $—C_2F_5$, $—C_3F_7$, or a mixture thereof. Another suitable perfluoro(alkyl vinyl ether) is 2,2-bis(trifluoromethyl)-4,5-difluoro-1,3-dioxole (PDD). Other suitable copolymers include copolymers of PDD. Teflon® AF is a family of amorphous fluoropolymers based on PDD. A typical Teflon® AF is a copolymer of tetrafluoroethylene and PDD.

The portion of the reactor wall fabricated from such polymeric materials may be limited to a fraction of the reactor wall (e.g., a window of the polymeric material positioned in a reactor principally fabricated from another material) or may constitute all or essentially all of the reactor wall (e.g., a tube reactor fabricated from the polymeric material).

Perfluoro(alkyl vinyl ether) copolymers have excellent chemical resistance, low surface energy, low flammability, low moisture adsorption, excellent weatherability and high continuous use temperature. In addition, they are among the purest polymer materials and are widely used in the semiconductor industry. They are also excellent for UV-vis transmission. For instance, a film of PFA copolymer having a thickness of 0.025 mm has transmission of 91-96% for visible light between 400 to 700 nm and transmission of 77-91% for UV light between 250 to 400 nm. Teflon® AF is also melt-processable. Due to its amorphous quality, Teflon® AF has superior transparency across the entire spectrum from the UV to the near IR.

A suitable photochlorination apparatus includes a reactor in which light having a suitable wavelength (e.g., from about 250 nm to about 400 nm) can irradiate the reaction components for a time sufficient to convert at least a portion of the starting materials to one or more compounds having a higher chlorine content. The reactor may be, for example, a tubular reactor fabricated from perfluoro(alkyl vinyl ether) copolymer (e.g., either a coil or extended tube), or tank fabricated from perfluoro(alkyl vinyl ether) copolymer, or a tube or tank fabricated from an opaque material which has a window fabricated from perfluoro(alkyl vinyl ether) copolymer. Typically, the thickness of the perfluoro(alkyl vinyl ether) copolymer is sufficient to permit transmittance of the light of sufficient intensity to promote the reaction (e.g., 0.02 mm to 1 mm). Where additional structural reinforcement is desired while maintaining the chemical resistance offered by the perfluoro(alkyl vinyl ether) copolymer, a layer of reinforcing material fabricated from a highly transmitting material (e.g., quartz) or a mesh of transmitting or opaque material may be used outside of the perfluoro(alkyl vinyl ether) copolymer layer.

The apparatus also includes a light source. The light source may be any one of a number of arc or filament lamps known in the art. The light source is situated such that light having the desired wavelength may introduced into the reaction zone (e.g., a reactor wall or window fabricated from a perfluoro (alkyl vinyl ether) copolymer and suitably transparent to light having a wavelength of from about 250 nm to about 400 nm).

Ordinarily the apparatus also includes a chlorine ($Cl_2$) source and a source of the material to be chlorinated. The chlorine source may be, for example, a cylinder containing chlorine gas or liquid, or equipment that produces chlorine (e.g., an electrochemical cell) that is connected to the reactor. The source of the material to be chlorinated may be, for example, a cylinder or pump fed from a tank containing the material, or a chemical process that produces the material to be chlorinated.

Of note are processes in accordance with this invention for increasing the chlorine content of at least one compound selected from hydrocarbons and halohydrocarbons; processes in accordance with this invention for increasing the fluorine content of at least one compound selected from hydrocarbons and halohydrocarbons; and processes in accordance with this invention for producing at least one olefinic compound from a hydrocarbon or halohydrocarbon containing at least two carbon atoms and at least two hydrogen atoms. As described more fully below, all of these processes involve reaction with chlorine in the presence of light.

Increasing Chlorine Content

Included in this invention is a process for increasing the chlorine content of a halogenated hydrocarbon compound or a hydrocarbon compound by reacting said compound with chlorine ($Cl_2$) in the presence of light.

Halogenated hydrocarbon compounds suitable as starting materials for the chlorination process of this invention may be saturated or unsaturated. Saturated halogenated hydrocarbon compounds suitable for the chlorination processes of this invention include those of the general formula $C_nH_aBr_b\text{-}Cl_cF_d$, wherein n is an integer from 1 to 4, a is an integer from 1 to 9, b is an integer from 0 to 4, c is an integer from 0 to 9, d is an integer from 0 to 9, the sum of b, c and d is at least 1 and the sum of a, b, c, and d is equal to 2n+2. Saturated hydrocarbon compounds suitable for chlorination are those which have the formula $C_qH_r$, where q is an integer from 1 to 4 and r is 2q+2. Unsaturated halogenated hydrocarbon compounds suitable for the chlorination processes of this invention include those of the general formula $C_pH_eBr_fCl_gF_h$, wherein p is an integer from 2 to 4, e is an integer from 0 to 7, f is an integer from 0 to 2, g is an integer from 0 to 8, h is an integer from 0 to 8, the sum of f, g and h is at least 1 and the sum of e, f, g, and h is equal to 2p. Unsaturated hydrocarbon compounds suitable for chlorination are those which have the formula $C_iH_j$ where i is an integer from 2 to 4 and j is 2i. The chlorine content of saturated compounds of the formula $C_nH_aBr_bCl_cF_d$ and $C_qH_r$, and/or unsaturated compounds of the formula $C_pH_eBr_fCl_gF_h$ and $C_iH_j$ may be increased by reacting said compounds with $Cl_2$ in the vapor phase in the presence of light. Such a process is referred to herein as a photochlorination reaction.

The photochlorination of the present invention may be carried out in either the liquid or the vapor phase. For vapor phase photochlorination, initial contact of the starting materials with $Cl_2$ may be a continuous process in which one or more starting materials are vaporized (optionally in the presence of an inert carrier gas, such as nitrogen, argon, or helium) and contacted with chlorine vapor in a reaction zone. A suitable photochlorination reaction zone is one in which light having a wavelength of from about 300 nm to about 400 nm can irradiate the reaction components for a time sufficient to convert at least a portion of the starting materials to one or more compounds having a higher chlorine content. The source of light may be any one of a number of arc or filament lamps known in the art. Light having the desired wavelength may introduced into the reaction zone by a number of means. For example, the light may enter the reaction zone through a lamp well or window fabricated from a perfluoro(alkyl vinyl ether) copolymer suitably transparent to light having a wavelength of from about 300 nm to about 400 nm. Likewise, the walls of the reaction zone may be fabricated from such a material so that at least a portion of the light used for the photochlorination can be transmitted through the walls.

Alternatively, the process of the invention may be carried out in the liquid phase by feeding $Cl_2$ to a reactor containing the starting materials. Suitable liquid phase reactors include vessels fabricated from a perfluoro(alkyl vinyl ether) copolymer in which an external lamp is directed toward the reactor and metal, glass-lined metal or fluoropolymer-lined metal reactors having one or more wells or windows fabricated from a perfluoro(alkyl vinyl ether) copolymer for introducing light having a suitable wavelength. Preferably the reactor is provided with a condenser or other means of keeping the starting materials in the liquid state while permitting the hydrogen chloride (HCl) released during the chlorination to escape the reactor.

In some embodiments it may be advantageous to conduct the photochlorination in the presence of a solvent capable dissolving one or more of the starting materials and/or chlorination products. Preferred solvents include those that do not have easily replaceable hydrogen substituents. Examples of solvents suitable for step (a) include carbon tetrachloride, 1,1-dichlorotetrafluoroethane, 1,2-dichlorotetrafluoroethane, 1,1,2-trichlorotrifluoroethane, benzene, chlorobenzene, dichlorobenzene, fluorobenzene, and difluorobenzene.

Suitable temperatures for the photochlorination of the starting materials of the formula are typically within the range of from about −20° C. to about 60° C. Preferred temperatures are typically within the range of from about 0° C. to about 40° C. In the liquid phase embodiment, it is convenient to control the reaction temperature so that starting material is primarily in the liquid phase; that is, at a temperature that is below the boiling point of the starting material(s) and product(s).

The pressure in a liquid phase process is not critical so long as the liquid phase is maintained. Unless controlled by means of a suitable pressure-regulating device, the pressure of the system increases as hydrogen chloride is formed by replacement of hydrogen substituents in the starting material by chlorine substituents. In a continuous or semi-batch process it is possible to set the pressure of the reactor in such a way that the HCl produced in the reaction is vented from the reactor (optionally through a packed column or condenser). Typical reactor pressures are from about 14.7 psig (101.3 kPa) to about 50 psig (344.6 kPa).

The amount of chlorine ($Cl_2$) fed to the reactor is based on whether the starting material(s) to be chlorinated is(are) saturated or unsaturated, and the number of hydrogens in $C_nH_aBr_bCl_cF_d$, $C_qH_r$, $C_pH_eBr_fCl_gF_h$, and $C_iH_j$ that are to be replaced by chlorine. One mole of $Cl_2$ is required to saturate a carbon-carbon double bond and a mole of $Cl_2$ is required for every hydrogen to be replaced by chlorine. A slight excess of chlorine over the stoichiometric amount may be necessary for practical reasons, but large excesses of chlorine will result in complete chlorination of the products. The ratio of $Cl_2$ to halogenated carbon compound is typically from about 1:1 to about 10:1.

Specific examples of photochlorination reactions of saturated halogenated hydrocarbon compounds of the general formula $C_nH_aBr_bCl_cF_d$ and saturated hydrocarbon compounds of the general formula $C_qH_r$ which may be carried out in accordance with this invention include the conversion of $C_2H_6$ to a mixture containing $CH_2ClCCl_3$, the conversion of $CH_2ClCF_3$ to a mixture containing $CHCl_2CF_3$, the conversion of $CCl_3CH_2CH_2Cl$, $CCl_3CH_2CHCl_2$, $CCl_3CHClCH_2Cl$ or $CHCl_2CCl_2CH_2Cl$ to a mixture containing $CCl_3CCl_2CCl_3$, the conversion of $CH_2FCF_3$ to a mixture containing $CHClFCF_3$ and $CCl_2FCF_3$, the conversion of $CH_3CHF_2$ to $CCl_3CClF_2$, the conversion of $CF_3CHFCHF_2$ to a mixture containing $CF_3CClFCHF_2$ and $CF_3CHFCClF_2$, and the conversion of $CF_3CH_2CHF_2$ to $CF_3CH_2CClF_2$.

Specific examples of photochlorination reactions of unsaturated halogenated hydrocarbon compounds of the general formula $C_pH_eBr_fCl_gF_h$ and unsaturated hydrocarbon compounds of the general formula $C_iH_j$ which may be carried out in accordance with this invention include the conversion of $C_2H_4$ to a mixture containing $CH_2ClCH_2Cl$, the conversion of $C_2Cl_4$ to a mixture containing $CCl_3CCl_3$, the conversion of $C_3H_6$ a mixture containing $CCl_3CCl_2CCl_3$, and the conversion of $CF_3CCl=CCl_2$ to a mixture containing $CF_3CCl_2CCl_3$.

Of note is a photochlorination process for producing a mixture containing 2-chloro-1,1,1-trifluoroethane (i.e., $CH_2ClCF_3$ or HCFC-133a) by reaction of $CH_3CF_3$ with $Cl_2$ in the vapor phase in the presence of light in accordance with this invention. Also of note is a catalytic process for producing a mixture containing 1,2,2-trichloro-1,1,3,3,3-pentafluoropropane (i.e., $CClF_2CCl_2CF_3$ or CFC-215aa) or 1,2-dichloro-1,1,1,3,3,3-hexafluoropropane (i.e., $CClF_2CClFCF_3$ or CFC-216ba) by the chlorination of a corresponding hexahalopropene of the formula $C_3Cl_{6-x}F_x$, wherein x equals 5 or 6.

Contact times of from 0.1 to 60 seconds are typical; and contact times of from 1 to 30 seconds are often preferred.

Mixtures of saturated hydrocarbon compounds and saturated halogenated hydrocarbon compounds and mixtures of unsaturated hydrocarbon compounds and unsaturated halogenated hydrocarbon compounds as well as mixtures comprising both saturated and unsaturated compounds may be chlorinated in accordance with the present invention. Specific examples of mixtures of saturated and unsaturated hydrocarbons and halogenated hydrocarbons that may be used include a mixture of $CCl_2=CCl_2$ and $CCl_2=CClCCl_3$, a mixture of $CHCl_2CCl_2CH_2Cl$ and $CCl_3CHClCH_2Cl$, a mixture of $CHCl_2CH_2CCl_3$ and $CCl_3CHClCH_2Cl$, a mixture of $CHCl_2CHClCCl_3$, $CCl_3CH_2CCl_3$, and $CCl_3CCl_2CH_2Cl$, a mixture of $CHF_2CH_2CF_3$ and $CHCl=CHCF_3$, and a mixture of $CH_2=CH_2$ and $CH_2=CHCH_3$.

Increasing the Fluorine Content

Included in this invention is a process for a halogenated hydrocarbon compound or a hydrocarbon compound by reacting said compound with chlorine ($Cl_2$) in the presence of light as described above; and then reacting the halogenated hydrocarbon produced with hydrogen fluoride. Fluorination reactions are well known in the art. They can be conducted both in either the vapor phase or liquid phase using a variety of fluorination catalysts. See for example, Milos Hudlicky, Chemistry of Organic Fluorine Compounds $2^{nd}$ (Revised Edition), pages 91 to 135 and references cited therein (Ellis Harwood-Prentice Hall Publishers, 1992). Of note are vapor phase fluorinations in the presence of a fluorination catalyst. Preferred fluorination catalysts include chromium catalysts (e.g., $Cr_2O_3$ by itself of with other metals such as magnesium halides or zinc halides on $Cr_2O_3$); chromium(III) halides supported on carbon; mixtures of chromium and magnesium (including elemental metals, metal oxides, metal halides, and/or other metal salts) optionally on graphite; and mixtures of chromium and cobalt (including elemental metals, metal oxides, metal halides, and/or other metal salts) optionally on graphite, alumina, or aluminum halides such as aluminum fluoride.

Fluorination catalysts comprising chromium are well known in the art (see e.g., U.S. Pat. No. 5,036,036). Chromium supported on alumina can be prepared as described in U.S. Pat. No. 3,541,834. Chromium supported on carbon can be prepared as described in U.S. Pat. No. 3,632,834. Fluorination catalysts comprising chromium and magnesium may be prepared as described in Canadian Patent No. 2,025,145. Other metals and magnesium optionally on graphite can be prepared in a similar manner to the latter patent.

Preferred chromium fluorination catalysts comprise trivalent chromium. Of note is $Cr_2O_3$ prepared by pyrolysis of $(NH_4)_2Cr_2O_7$, $Cr_2O_3$ having a surface area greater than about 200 $m^2/g$, and $Cr_2O_3$ prepared by pyrolysis of $(NH_4)_2Cr_2O_7$ or having a surface area greater than about 200 $m^2/g$ some of which are commercially available.

Halogenated hydrocarbon compounds suitable for the fluorination of this invention include saturated compounds of the general formula $C_mH_wBr_xCl_yF_z$, wherein m is an integer from 1 to 4, w is an integer from 0 to 9, x is an integer from 0 to 4, y is an integer from 1 to 10, z is an integer from 0 to 9, and the sum of w, x, y, and z is equal to 2n+2.

Examples of saturated compounds of the formula $C_mH_wBr_xCl_yF_z$ which may be reacted with HF in the presence of a catalyst include $CH_2Cl_2$, $CHCl_3$, $CCl_4$, $C_2Cl_6$, $C_2BrCl_5$, $C_2Cl_5F$, $C_2Cl_4F_2$, $C_2Cl_3F_3$, $C_2Cl_2F_4$, $C_2ClF_5$, $C_2HCl_5$, $C_2HCl_4F$, $C_2HCl_3F_2$, $C_2HCl_2F_3$, $C_2HClF_4$, $C_2HBrF_4$, $C_2H_2Cl_4$, $C_2H_2Cl_3F$, $C_2H_2Cl_2F_2$, $C_2H_2ClF_3$, $C_2H_3Cl_3$, $C_2H_3Cl_2F$, $C_2H_3ClF_2$, $C_2H_4Cl_2$, $C_2H_4ClF$, $C_3Cl_6F_2$, $C_3Cl_5F_3$, $C_3Cl_4F_4$, $C_3Cl_3F_5$, $C_3HCl_7$, $C_3HCl_6F$, $C_3HCl_5F_2$, $C_3HCl_4F_3$, $C_3HCl_3F_4$, $C_3HCl_2F_5$, $C_3H_2Cl_6$, $C_3H_2BrCl_5$, $C_3H_2Cl_5F$, $C_3H_2Cl_4F_2$, $C_3H_2Cl_3F_3$, $C_3H_2Cl_2F_4$, $C_3H_2ClF_5$, $C_3H_3Cl_5$, $C_3H_3Cl_4F$, $C_3H_3Cl_3F_2$, $C_3H_3Cl_2F_3$, $C_3H_3ClF_4$, $C_3H_4Cl_4$, $C_4Cl_4Cl_4$, $C_4Cl_4Cl_6$, $C_4H_5Cl_5$ and $C_4H_5Cl_4F$.

Of note is a process for producing 1,1,1,2,2-pentafluoroethane (i.e., $CHF_2CF_3$ or HFC-125) by the photochlorination of 1,1,1,2 tetrafluoroethane (i.e., $CH_2FCF_3$ or HFC-134a) to produce 2-chloro-1,1,1,2 tetrafluoroethane (i.e., $CHClFCF_3$ or HCFC-124); and the fluorination of the HCFC-124 to produce HFC-125. HFC-125 may also be produced by the photochlorination of 1,1,2,2 tetrafluoroethane (i.e., $CHF_2CHF_2$ or HFC-134) to produce 2-chloro-1,1,2,2 tetrafluoroethane (i.e., $CClF_2CHF_2$ or HCFC-124a); and fluorination of the HCFC-124a to produce HFC-125. Also of note is a process for producing 1,1,1,3,3,3-hexafluoropropane ($CF_3CH_2CF_3$ or HFC-236fa) by the photochlorination of 1,1,1,3,3-pentafluoropropane ($CF_3CH_2CHF_2$ or HFC-245fa) to produce 3-chloro-1,1,1,3,3-pentafluoropropane (i.e., $CF_3CH_2CClF_2$ or HCFC-235fa); and fluorination of the HCFC-235fa to produce HFC-236fa. Further discussion of producing HFC-236fa by fluorination is provided in U.S. Patent Application No. 60/638,277 which was filed Dec. 22, 2004, and is incorporated herein by reference.

In one embodiment of the invention, the photochlorination and further fluorination can be conducted in situ and the fluorinated product(s) recovered. In a second embodiment, the effluent from the photochlorination step may be fed to a second reactor for fluorination. The photochlorination product mixture can be fed to a fluorination reactor with or without prior separation of the products from the photochlorination reactor. Of note are processes where the photochlorination product mixture is directly fed to a fluorination reactor without prior separation of the products from the photochlorination reactor. In a third embodiment, HF can be fed together with chlorine and the other photochlorination starting materials to the photochlorination reactor and the effluent from the photochlorination reactor can be directed to a fluorination zone optionally containing a fluorination catalyst; and additional HF, if desired, can be fed to the fluorination zone.

Producing Olefins

Included in this invention is a process for producing an olefin from a halogenated hydrocarbon compound or a hydrocarbon compound by reacting said compound with chlorine ($Cl_2$) in the presence of light as described above; and then subjecting the halogenated hydrocarbon produced by the photochlorination to dehydrohalogenation. Dehydrohalogenation reactions are well known in the art. They can be conducted both in either the vapor phase or liquid phase using a variety of catalysts. See for example, Milos Hudlicky, Chemistry of Organic Fluorine Compounds $2^{nd}$ (Revised Edition), pages 489 to 495 and references cited therein (Ellis Harwood-Prentice Hall Publishers, 1992). Of note are vapor phase dehydrohalogenations in the presence of a catalyst. Suitable catalysts for dehydrohalogenation include carbon, metals (including elemental metals, metal oxides, metal halides, and/or other metal salts); alumina; fluorided alumina; aluminum fluoride; aluminum chlorofluoride; metals supported on alumina; metals supported on aluminum fluoride or chlorofluoride; magnesium fluoride supported on aluminum fluoride; metals supported on fluorided alumina; alumina supported on carbon; aluminum fluoride or chlorofluoride supported on carbon; fluorided alumina supported on carbon; metals supported on carbon; and mixtures of metals, aluminum fluoride or chlorofluoride, and graphite. Suitable metals for use on catalysts (optionally on alumina, aluminum fluoride, aluminum chlorofluoride, fluorided alumina, or carbon) include chromium, iron, and lanthanum. Preferably when used on a support, the total metal content of the catalyst will be from about 0.1 to 20 percent by weight; typically from about 0.1 to 10 percent by weight. Preferred catalysts for dehydrohalogenation include carbon, alumina, and fluorided alumina.

Halogenated hydrocarbon compounds suitable for the dehydrohalogenation of this invention include saturated compounds of the general formula $C_mH_wBr_xCl_yF_z$, wherein m is an integer from 2 to 4, w is an integer from 1 to 9, x is an integer from 0 to 4, y is an integer from 1 to 9, z is an integer from 0 to 8, and the sum of w, x, y, and z is equal to 2n+2. The compound photochlorinated to produce the compound subjected to dehydrohalogenation (e.g., a saturated compound of the formula $C_nH_aBr_bCl_cF_d$ or a saturated compound of the formula $C_qH_r$ as described above) should contain at least two carbon atoms and two hydrogen atoms (e.g., for said compounds of the formulas $C_nH_aBr_bCl_cF_d$ and $C_qH_r$, w, n, a and q should be at least 2). Of note are processes where the compound photochlorinated is a halogenated hydrocarbon that contains fluorine Of note is a process for producing 1,1-difluoroethylene (i.e., $CF_2=CH_2$ or vinylidene fluoride) by the photochlorination of 1,1-difluoroethane (i.e., $CHF_2CH_3$ or HFC-152a) to produce 1-chloro-1,1-difluoroethane (i.e., $CClF_2CH_3$ or HCFC-142b); and the dehydrohalogenation of the HCFC-142b to produce 1,1-difluoroethylene. Also of note is a process for producing tetrafluoroethylene (i.e., $CF_2=CF_2$) by the photochlorination of 1,1,2,2-tetrafluoroethane (i.e., $CHF_2CHF_2$ or HFC-134) to produce 2-chloro-1,1,2,2-tetrafluoroethane (i.e., $CClF_2CHF_2$ or HCFC-124a); and the dehydrohalogenation of the HCFC-124a to produce tetrafluoroethylene. Also of note is a process for producing hexafluoropropylene ($CF_3CF=CF_2$) by the photochlorination of 1,2-dihydrohexafluoropropane (i.e., $CF_3CHFCHF_2$ or HFC-236ea) to produce 1-chloro-1,1,2,3,3,3-hexafluoropropane (i.e., $CF_3CHFCClF_2$ or HCFC-226ea); and dehydrohalogenation of the HCFC-226ea to produce hexafluoropropylene.

EXAMPLES

General Procedure for Chlorination and Product Analysis

Photochlorination was carried out using a 110 volt/275 watt sunlamp placed (unless otherwise specified) at a distance of 0.5 inches (1.3 cm) from the outside of the first turn of the inlet end of a coil of fluoropolymer tubing material through which the materials to be chlorinated were passed. The fluoropolymer tubing used in the examples below was a 36 inch (91.4 cm) long PFA tube (0.25 inch (0.6 cm) OD×0.126 inch (0.32 cm) ID) which was coiled to a diameter of 5.5 inches (14 cm) and contained suitable feed and exit ports. The organic feed material and chlorine were fed to the tubing using standard flow-measuring devices. The gas mixture inside was exposed to light generated by the sunlamp. The experiments were conducted at ambient temperature (about 23° C.) and under about atmospheric pressure. Organic feed material entering the tubing and the product after photochlorination were analyzed on-line using a GC/MS. The results are reported in mole %. 1.0 sccm (standard cubic centimeter per minute) is equal to about $1.7(10)^{-8}$ cubic meters per second.

Example 1

Photochlorination of HFC-245fa

HFC-245fa was analyzed prior to chlorination to have a purity of 99.8%. Feed gases consisting of HFC-245fa at a flow rate of 20.0 sccm and chlorine gas at a flow rate of 20.0 sccm were introduced into the PFA tubing. After exposure to light for one hour, the product was analyzed and found to contain 12.4 mole % of HFC-245fa, 87.2 mole % of HCFC-235fa, and 0.4 mole % of other unidentified compounds.

Example 2

Photochlorination of HFC-245fa

HFC-245fa was analyzed prior to chlorination to have a purity of 99.8%. Feed gases consisting of HFC-245fa at a flow rate of 20.0 sccm and chlorine gas at a flow rate of 40.0 sccm were introduced into the PFA tubing. After exposure to light for one hour, the product was analyzed and found to contain 10.7 mole % of HFC-245fa, 88.8 mole % of HCFC-235fa, and 0.5 mole % of other unidentified compounds.

Example 3

Photochlorination of HFC-245fa

HFC-245fa was analyzed prior to chlorination to have a purity of 99.8%. Feed gases consisting of HFC-245fa at a flow rate of 10.0 sccm and chlorine gas at a flow rate of 30.0 sccm were introduced into the PFA tubing. After exposure to light for one hour, the product was analyzed and found to contain 4.5 mole % of HFC-245fa, 94.8 mole % of HCFC-235fa, and 0.7 mole % of other unidentified compounds.

What is claimed is:

1. A process for increasing the fluorine content of $CF_3CH_2CHF_2$, comprising:
    (a) photochlorinating $CF_3CH_2CHF_2$ in a reactor in which light from a light source is directed through a wall of said reactor to interact with $CF_3CH_2CHF_2$ and chlorine in said reactor to produce $CF_3CH_2CClF_2$; and
    (b) reacting $CF_3CH_2CClF_2$ produced by the photochlorination in (a) with HF to produce $CF_3CH_2CF_3$;
    wherein the light directed through the reactor wall in (a) is directed through a copolymer of a perfluoro(alkyl vinyl ether); and $CF_3CH_2CHF_2$ and chlorine is reacted in the presence of light directed through said copolymer.

2. The process of claim 1 wherein said copolymer is a copolymer of at least one perfluorinated alkylene monomer with a perfluoro(alkyl vinyl ether).

3. The process of claim 2 wherein said copolymer is a copolymer of tetrafluoroethylene with a perfluoro(alkyl vinyl ether).

4. The process of claim 1 wherein said perfluoro(alkyl vinyl ether) is selected from the group consisting of $CF_3OCF=CF_2$, $C_2F_5OCF=CF_2$, $C_3F_7OCF=CF_2$, and mixtures thereof.

5. The process of claim 1 wherein said perfluoro(alkyl vinyl ether) is 2,2-bis(trifluoromethyl)-4,5-difluoro-1,3-dioxole.

6. The process of claim 1 wherein said copolymer is an amorphous copolymer of tetrafluoroethylene and 2,2-bis(trifluoromethyl)-4,5-difluoro-1,3-dioxole.

7. A process for increasing the fluorine content of $CF_3CH_2F$, comprising:
    (a) photochlorinating $CF_3CH_2F$ in a reactor in which light from a light source is directed through a wall of said reactor to interact with $CF_3CH_2F$ and chlorine in said reactor to produce $CF_3CHClF$; and
    (b) reacting $CF_3CHClF$ produced by the photochlorination in (a) with HF to produce $CF_3CHF_2$;
    wherein the light directed through the reactor wall in (a) is directed through a copolymer of a perfluoro(alkyl vinyl ether); and $CF_3CH_2F$ and chlorine is reacted in the presence of light directed through said copolymer.

8. The process of claim 7 wherein said copolymer is a copolymer of at least one perfluorinated alkylene monomer with a perfluoro(alkyl vinyl ether).

9. The process of claim 8 wherein said copolymer is a copolymer of tetrafluoroethylene with a perfluoro(alkyl vinyl ether).

10. The process of claim 7 wherein said perfluoro(alkyl vinyl ether) is selected from the group consisting of $CF_3OCF=CF_2$, $C_2F_5OCF=CF_2$, $C_3F_7OCF=CF_2$, and mixtures thereof.

11. The process of claim 7 wherein said perfluoro(alkyl vinyl ether) is 2,2-bis(trifluoromethyl)-4,5-difluoro-1,3-dioxole.

12. The process of claim 7 wherein said copolymer is an amorphous copolymer of tetrafluoroethylene and 2,2-bis(trifluoromethyl)-4,5-difluoro-1,3-dioxole.

13. A process for increasing the fluorine content of $CHF_2CHF_2$, comprising:
    (a) photochlorinating $CHF_2CHF_2$ in a reactor in which light from a light source is directed through a wall of said reactor to interact with $CHF_2CHF_2$ and chlorine in said reactor to produce $CHF_2CClF_2$; and
    (b) reacting $CHF_2CClF_2$ produced by the photochlorination in (a) with HF to produce $CF_3CHF_2$;
    wherein the light directed through the reactor wall in (a) is directed through a copolymer of a perfluoro(alkyl vinyl ether); and $CHF_2CHF_2$ and chlorine is reacted in the presence of light directed through said copolymer.

14. The process of claim 13 wherein said copolymer is a copolymer of at least one perfluorinated alkylene monomer with a perfluoro(alkyl vinyl ether).

15. The process of claim 14 wherein said copolymer is a copolymer of tetrafluoroethylene with a perfluoro(alkyl vinyl ether).

16. The process of claim 13 wherein said perfluoro(alkyl vinyl ether) is selected from the group consisting of $CF_3OCF=CF_2$, $C_2F_5OCF=CF_2$, $C_3F_7OCF=CF_2$, and mixtures thereof.

17. The process of claim 13 wherein said perfluoro(alkyl vinyl ether) is 2,2-bis(trifluoromethyl)-4,5-difluoro-1,3-dioxole.

18. The process of claim 13 wherein said copolymer is an amorphous copolymer of tetrafluoroethylene and 2,2-bis(trifluoromethyl)-4,5-difluoro-1,3-dioxole.

* * * * *